United States Patent [19]

Michaels

[11] 4,182,330
[45] Jan. 8, 1980

[54] MEANS FOR ADMINISTERING AMPHIPATHIC MEDICAMENT

[75] Inventor: Alan S. Michaels, Atherton, Calif.

[73] Assignee: Alza Corporation, Palo Alto, Calif.

[21] Appl. No.: 818,292

[22] Filed: Jul. 25, 1977

[51] Int. Cl.² ............................................. A61M 37/00
[52] U.S. Cl. ...................................... 128/260; 424/15
[58] Field of Search ................................ 128/260–268, 128/222; 424/15

[56] References Cited

U.S. PATENT DOCUMENTS

| | | | |
|---|---|---|---|
| 3,845,770 | 11/1974 | Theeuves et al. | 128/260 |
| 3,926,188 | 12/1975 | Baker et al. | 128/260 |
| 3,952,741 | 4/1976 | Baker | 128/260 |
| 4,008,719 | 2/1977 | Theeuves et al. | 128/260 |
| 4,014,334 | 3/1977 | Theeuves et al. | 128/260 |
| 4,036,227 | 7/1977 | Zaffaroni et al. | 128/260 |

OTHER PUBLICATIONS

*The Pharmacological Basis of Therapeutics*, 1970, 4th Ed., pp. 677-708.
*Pharmaceutical Sciences*, 1970, 14th Ed., pp. 858-864.

*Primary Examiner*—Robert W. Michell
*Assistant Examiner*—C. F. Rosenbaum
*Attorney, Agent, or Firm*—Paul L. Sabatine; Thomas E. Ciotti; Edward L. Mandell

[57] ABSTRACT

Means for administering an amphipathic medicament by micelle solubilization is disclosed. The micelle consists of a nonionic surfactant medicament adduct. The adduct is coated onto an osmotically effective solute and housed in an osmotic therapeutic system for administering the medicament in a therapeutically effective amount over a prolonged period of time.

9 Claims, 2 Drawing Figures

MEANS FOR ADMINISTERING AMPHIPATHIC MEDICAMENT

FIELD OF THE INVENTION

The present invention pertains to an osmotic dosage formulation useful for administering amphipathic medicaments.

BACKGROUND OF THE INVENTION

Many valuable medicaments widely used by the medical and veterinary professions are known to possess amphipathic properties. This property, of solvent-attracting and solvent-repelling within a single medicament, severely restricts both the medicament's formulation into operable dosage forms and its administration in a controlled and continuous manner for obtaining its beneficial effects. For example, one valuable class of medicaments exhibiting nonionic amphipathic properties are cardiac acting digitaloid drugs. These drugs have as their major pharmacological action the ability to effect cardiovascular functions and they are therefore widely used for the management of heart conditions. The drugs are used to improve heart muscle activity and tone, and for treating congestive heart failure. The digitaloid drugs commonly used for the present purpose are often referred to as cardiac glycosides. While these drugs possess beneficial properties, their amphipathic properties are shortcomings associated with their use. For example, drugs such as digoxin, the cardiotonic glycoside obtained from Digitalis lanata, and with digitoxin, the cardiotonic glycoside from Digitalis purpurea, their insolubility in water and their limited solubility in organic carriers restricts manufacturing the drugs into formulations suitable for administering them in a controlled and continuous manner. The prior art attempted to improve on their administration by mixing the drugs with cocoa-butter, solidified glycerine and paraffin wax, but this has not lead to true controlled formulations. See *The Pharmacological Basis of Therapeutics*, by Goodman and Gilman, 4th Ed., pages 677 to 708, 1970, published by the MacMillian Company, New York; and *Pharmaceutical Sciences* by Remington, 14th Ed., pages 858 to 864, 1970, published by Mack Publishing Company, Easton, Pennsylvania. It will be appreciated by those versed in the present art, that in view of the above presentation, a critical need exists for a means for administering amphipathic drugs, and if such were made available it would represent a valuable and useful contribution to the practicing art.

OBJECTS OF THE INVENTION

Accordingly, it is an immediate object of this invention to provide a novel and useful means for administering amphipathic medicaments which means overcomes the shortcomings associated with the prior art.

Another immediate object of the invention is to provide a dosage form that can administer in a controlled and continuous manner medicaments possessing both hydrophilic and hydrophobic properties.

A further object of this invention is to provide an osmotic dosage form useful for dispensing amphiphilic medicaments for the treatment of their intended effects.

Still a further object of the invention is to administer drug by micellar solubilization which micelle consists of a amphipathic drug/nonionic adduct and is administrable by an osmotic therapeutic system over a prolonged period of time.

Another object of the invention is to provide a pharmaceutical formulation useful for administering digitaloid drugs in a controlled and continuous manner over a prolonged period of time.

A further object of the invention is to provide an osmotic dosage form useful for dispensing cardiac glycosides for the treatment of cardiac decompensation.

Yet a further object of the invention is to provide an oral osmotic therapeutic system useful for administering digitaloid drugs to a warm-blooded animal including humans at a controlled and continuous rate over a prolonged period of time.

Other objects and advantages of the present invention will become more apparent from the following detailed description of the invention and the appended claims defining the scope thereof.

SUMMARY OF THE INVENTION

The invention concerns a pharmaceutical formulation comprising an amphipathic drug such as a cardiac glycoside drug, capable of administration over a prolonged period of time. The formulation comprises a micellar aggregate consisting of a drug/nonionic surfactant adduct, which adduct is coated onto an osmotically effective solute. The formulation is charged into an oral osmotic system and the drug is dispensed therefrom.

DETAILED DESCRIPTION OF THE DISCLOSURE

Figure 1:
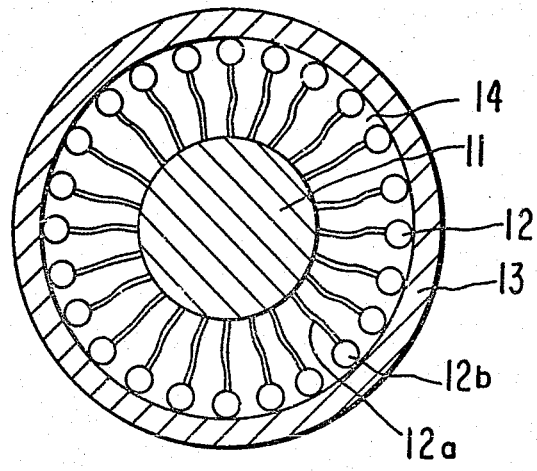

In accordance with the practice of the present invention, it has now been found that amphipathic drugs can be compounded into a formulation capable of administration from an osmotic therapeutic system into a predominantly aqueous, biological environment. The formulation consists essentially of a micellar aggregate of (1) the drug, and (2) a nonionic surfactant forming an adduct, which adduct is 3) coated onto an osmotically effective solute. The formulation is charged into the compartment of an oral osmotic therapeutic system. The system comprises a semipermeable wall surrounding the compartment with a passageway through the wall for releasing drug therefrom.

Exemplary drugs or medicaments that can be administered according to the spirit of the invention include locally and systemically acting drugs. These include a member selected from the group consisting of physiologically and pharmacologically effective drugs, such as central nervous system acting drugs, hypnotic, sedative, psychic energizer, tranquilizer, anticonvulsant, antiparkinson, muscle relaxant, analgesic, antipyretic, anti-inflammatory, anesthetic, antispasmodic, antimicrobial, antiviral, antiulcer, hormonal, sympathomimetic, diuretic, hypoglycemic, vitamin and ophthalmic drugs. The beneficial drugs and the dose amount for humans are known to the art in *Remington's Pharmaceutical Sciences*, 14th Ed., 1970, published by Mack Publishing Co., Easton, Penna., in *The Pharmacological Basis of Therapeutics*, by Goodman and Gilman, 4th Ed., 1970, published by the MacMillian Co., London, and in U.S. Pat. No. 3,977,404, which patent is assigned to the ALZA Corp. of Palo Alto, Calif., the assignee of this patent application.

A presently preferred class of drugs that can be administered according to the mode and manner of this invention are the digitaloid or cardiac glycoside drugs. The digitaloid or cardiac glycoside drugs that can be administered are the drugs characterized by the highly specific and powerful action which they exert upon the cardiac muscle. These drugs are valuable in the treatment of congestive heart failure due to heart disease or other causes. The drugs stimulate the heart to greater contractile activity and they restore the original tonicity. In physiological and pharmacological operations, the ventricles are more completely emptied, blood flow is increased in the heart, heart muscle nourishment is increased and becomes more efficient and heart size is decreased.

Exemplary cardiac glycoside for the present purpose include digitoxigenin; digitoxigenin-β-D-glucoside; digitoxin; digitoxigenin-β-tetracetyl-D-glucoside; acetyl digitoxin; desacetyldigilanide, digilanide, neriifolin; acetylneriifolin cerberin; thevetin; somalin; odoroside; honghelin; digoxigenin; digoxigenin-β-D-glucoside; digoxigenin-β-tetracetyl-D-glucoside; digoxin; acetyldigoxin; desacetyl digilanide; digilanide; gitoxin; α-acetyl gitoxin; desacetyl digilanide; oleandrin; desacetyloleandrin; dizitalinum verum; strospesid; strophanthidin; cymarin; cymarol; convallatoxin; cheirotoxin; convalloside; strophanthidin-acetate; perilogenin; periplocymarin; emicymarin; periplocin; uzarin; hellebrigenin; hellebrin; desglucohellebrin; scillarenin; proscillaridin; scillaren; scillirosidin; scilliroside; sarmentogenin; sarmentocymarin; ovabain, calotropin; and calotoxin. The presently preferred digitaloid drugs include acetyldigitoxin, deslanoside, digitalis, digitoxin, digoxin, getalin, lanatoside, and the mixture of lanatoside-A, lanatoside-B and lanatoside-C. The drugs can be administered in therapeutically effective amounts to produce the desired effect. Typical amounts include for rapid digitalization from 500 mcg to 4 mg divided into several administrations given within 24 hours, maintenance digitalization of 200 mcg to 1.5 mg daily with usual maintenance digitalization of 100 mcg to 300 mcg every 6 to 8 hours from 1 to 3 times a day or approximately 12 mcg to 50 mcg per hour. These drugs and the amount needed for producing the beneficial effect are disclosed in *Textbook of Organic Medicinal and Pharmaceutical Chemistry*, edited by Wilson, Gisvold and Doerge, pages 750 to 768, 1966, published by Lippincott Company, Philadelphia, Pennsylvania; and in *Pharaceutical Sciences*, 14th Ed., by Remington, pages 858 to 863, 1970.

Exemplary nontoxic, nonionic surfactants suitable for forming an adduct with a drug include alkylated aryl polyether alcohols commercially available as Triton ®, polyethylene glycol tertdodecyl thioether available as Nonic ®, fatty acid amide condensate or Alrosol ®, aromatic polyglycol ether condensate or Neutronyx ®, fatty acid alkanolamine condensate or Ninol ®, sorbitan monolaurate or Span ®, polyoxyethylene sorbitan esters or Tweens ®, sorbitan monolaurate polyoxyethylene or Tween 20 ®, sorbitan mono-oleate polyoxyethylene or Tween 80 ®, polyoxypropylenepolyoxyethylene or Pluronic ®, and polyoxypropylenepolyoxyethylene-8500 or Pluronic 68 ®. Generally, from 10 parts to 300 parts by weight of surfactant (per 100 parts by weight of drug) is admixed with the drug, leading to micellar solubilization of said drug in association with the surfactant to form the surfactant/drug adduct. The surfactants are commerically available and they are described in *Harry's Cosmeticology*, pages 401 to 407, 1973, published by Chemical Publishing Co., Inc., New York.

Exemplary osmotically effective solutes suitable for receiving a coating of the adduct on their surface include solutes that exhibit an osmotic pressure gradient across the semipermeable wall of an osmotic device against an external fluid. Solutes capable of imbibing external fluid into the compartment include magnesium sulfate, magnesium chloride, sodium chloride, lithium chloride, potassium sulfate, sodium carbonate, sodium sulfate, lithium bicarbonate, sodium sulfate, calcium sulfate, calcium lactate, mannitol, urea, inositol, magnesium succinate, raffinose, sucrose, glucotose and lactose. Generally, a 1.0 to 1000 μm (micrometers) layer of drug/surfactant adduct is coated onto the exposed surface of the osmotically effective solute particles, to form the drug-core formulation. Osmotically effective, nontoxic solutes are commercially available and they are known to the art in U.S. Pat. Nos. 3,732,865 and 3,880,164.

Exemplary semipermeable materials suitable for forming the wall of the osmotic system include those materials that do not adversely affect the drug and the host, and which materials are permeable to the passage of an external fluid such as water and essentially impermeable to the passage of drug. Typical materials include cellulose acetate, cellulose diacetate, cellulose triacetate, dimethyl cellulose acetate, cellulose acetate phthalate, cellulose acetate octate and the like. These materials are known to the art and they generally have a fluid permeability of 0.01 to 10 cc/cm X hour or day at atmospheric pressure. The materials are described in U.S. Pat. Nos. 3,760,805 and 3,760,806.

The following examples are illustrative of the present invention. In the examples, micellar solubilization of the amphipathic drug is affected by having drug in association with the nonionic surfactant to produce a drug/surfactant adduct, which adduct is coated onto the surface of an osmotic solute. The process produces a micellar aggregate in which the hydrophobic parts of the micelles are associated with hydrophilic parts of the drug-molecules, and the hydrophilic parts of the micelles are positioned on the outer micellar surfaces. The water-repellent part of the micelle is thus surrounded by a hydrophilic part thereby making the micelle essentially water-soluble and dispensible. The osmotic solute is coated with the micellar aggregate, providing the energy source needed to effect operation of the system. The examples should not be considered as limiting the scope of the invention, as these examples and other equivalents thereof will become apparent to those versed in the art in the light of the present disclosure and the accompanying claims.

EXAMPLES 1

A digitaloid formulation is prepared according to the following steps: (a) first, one part by weight of digoxin, the cardiac glycoside of digoxigenin, is dissolved in 200 parts by weight of an equi-volume mixture of 95% ethanol and chloroform at 45° C.; (b) then, one part by weight of polyoxyethylene sorbitan mono-oleate is added to (a) with constant stirring at 45° C. to yield a clear solution; (c) next, one drop of the solution prepared in (b) is placed on a clean, glass slide, and gently warmed to evaporate the solvent. Then, one drop of water is added to the slide, stirred, and the solution examined for precipitated solid. The solution should be free of solid, and if the solution yields a precipitate is should be discarded.

Next, (d), 100 parts by weight of mannitol, an osmotically effective solute, is added to a mixing bowl. The bowl is equipped with a hot air blower mounted over the bowl for directing a stream of hot air onto the mixing head. Then, (e), with strong agitation and the hot air blowing, 25 parts of the drug/surfactant solution prepared in (a) is slowly added to (d) the osmotic solute. The stirring is continued until all odor of solvent disappears. Next, (f), the powdered formulation consisting of drug/surfactant coated onto solute prepared in (e) is spread onto a shallow pan, placed in a vacuum oven at 30° to 40° and dried overnight.

Next, (g), about 250 mg of the adduct coated solute formulation of (f) is compressed in a conventional Manesty tableting machine using 5/16 inch diameter concave punch to produce compressed cores having a hardness of about 9 kg, measurable on a Strong-Cobb hardness tester. Each of the cores contain about 0.31 mg of digoxin, about half the normal daily maintenance dose. Then, (h), the cores prepared in (g) are placed in a Wurster air suspension machine and tumbled until they are uniformly coated with a semipermeable wall formed for a 5% cellulose acetate solution in dioxane. The coated systems are dried in an oven at 50° C. for one week to yield a wall 5-10 mils thick. Finally, a 5-10 mil diameter aperture is drilled through the wall.

The amount of drug released over a prolonged period of time can be controlled by regulating the thickness of the semipermeable wall and the diameter of the passageway of the system according to the teachings of U.S. Pat. Nos. 3,845,770 and 3,916,899. In the above preparation, one gram of the solute mannitol dissolves in 5.5 ml of water, and the concentration of the solubilized digoxin in solution released from the system can accordingly be regulated to 250 mcg/ml over a 6 to 8 hour period of time.

EXAMPLE 2

The procedure of Example 1 is repeated, except that the cardiac glycoside is a member selected from the group consisting of acetyldigitoxin, deslanoside, digitalis, digitoxin, gitalin, and lanatoside.

EXAMPLE 3

The procedures of Examples 1 and 2 are repeated with the conditions as described except that the non-ionic surfactant used to form the adduct is a member selected from the group consisting of polyoxyethylene sorbitan tristearate, polyethylene glycol tertdodecyl thioether, polyoxypropylene glycol (mol. wt. 1750) plus 160 moles of ethylene oxide, isooctyl phenoxy polyethoxyethanol, and polyoxypropylene glycol (mol. wt. 2050) plus 110 moles of ethylene oxide.

EXAMPLE 4

Figure 1A:
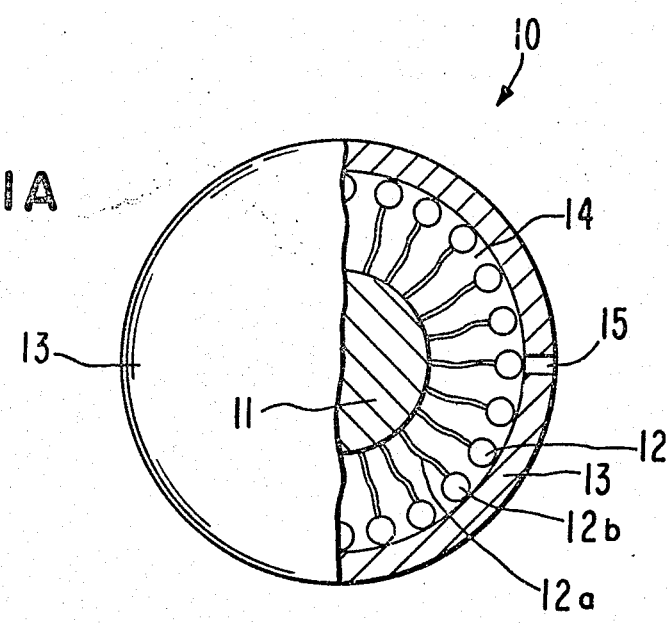

The procedure of Examples 1 through 3 are repeated in this example. This example illustrates the design of one embodiment of an osmotic therapeutic system, made according to the mode and manner of the invention, for administering amphipathic drug to a biological environment. The osmotic therapeutic system administers drug at a controlled rate over a prolonged period of time. In the example, FIG. 1 illustrates osmotic solute 11 coated with drug/surfactant adduct 12. Adduct 12 surrounds solute 11 with FIG. 1A illustrating osmotic therapeutic system 10, seen in opened section, housing solute 11 surrounded by adduct 12. System 10 is comprised of a shaped semipermeable wall 13 permeable to the passage of an external fluid, and substantially impermeable to the passage of drug, surfactant and solute. Wall 13 surrounds and forms compartment 14 housing 11 and 12. A passageway 15, in wall 13, communicates with compartment 14 for releasing drug to the exterior of system 10.

EXAMPLE 5

The procedure of the above examples is repeated in this example leading to the micellar solubilization of sparingly soluble drugs hydrocortisone, dexamethasone, testosterone and progesterone in association with long-chain polyoxyethylene non-ionic surfactants to form a micelle. Surfactants having various hydrophilic chain lengths including polyoxyethylated cetyl alcohols containing 17, 32, 44 and 63 mols of ethylene oxide can be used with the drugs leading to their uptake into micelles formed with the pharmaceutical surfactants. In FIGS. 1 and 1A surfactant micelle 12 is illustrated which offers a range of polarity from a non-polar hydrocarbon core 12A via the semipolar polyoxyethylene to the increasingly polar hydrated polyoxyethylene portion, to pure water on the micellar surface at polar head group 12. The micellar form is subsequently coated onto an osmotic solute 11 and charge into an osmotic therapeutic system 10.

The above disclosure is intended to be illustrative of the present invention, and the invention is not intended to be limited thereto. Those versed in the subject art can practice the invention from a reading of this disclosure, and more particularly in the light of the prior art exemplified by *Drill's Pharmacology in Medicine*, pages 567 to 593, 1965, published by McGraw-Hill Company, New York. Thus, since different embodiments of the invention may be made without departing from the scope thereof, these shall be interpreted as embraced by the invention.

I claim:

1. An osmotic therapeutic system for the controlled dispensing of drug to a biological environment of use, said system comprising:
   (a) a shaped wall formed of a non-toxic semipermeable material that maintains its integrity during the drug dispensing period and which material is permeable to the passage of an external fluid in the environment and substantially impermeable to the passage of drug, the wall surrounding and forming;
   (b) a compartment;
   (c) a micelle comprising an amphipathic drug pharmaceutically acceptable surfactant adduct which adduct is coated onto an osmotically effective solute that exhibits an osmotic pressure gradient across the wall against the fluid housed in the compartment;
   (d) a passageway in the wall communicating with the compartment and the exterior of the system, and;
   (e) wherein in operation when the system is in the environment, fluid from the environment is imbibed through the wall into the compartment in a tendency towards osmotic equilibrium at a rate determined by the permeability of the wall and the osmotic pressure gradient across the wall, thereby continuously forming a solution of adduct, which solution containing the drug is dispensed through the passageway at a controlled rate over a prolonged period of time.

2. The osmotic therapeutic system for the controlled dispensing of beneficial drug according to claim 1 wherein the drug is a member selected from the group consisting of locally and systemically acting drugs.

3. The osmotic therapeutic system for the controlled dispensing of beneficial drug according to claim 1, wherein the micelle is a micellar aggregate consisting essentially of an amphipathic drug and a nonionic surfactant.

4. The osmotic therapeutic system for the controlled dispensing of beneficial drug according to claim 1, wherein the amphipathic drug is a member selected from the group consisting of central nervous system, hypnotic, sedative, tranquilizer, anticonvulsant, antiparkinson, analgesic, anesthetic, antispasmodic, antiviral, antiulcer, hormonal and antimicrobial drugs.

5. The osmotic therapeutic system for the controlled dispensing of beneficial drug according to claim 1 wherein the micelle consists of 10 parts to 300 parts by weight of surfactant per 100 parts of drug.

6. The osmotic therapeutic system for the controlled dispensing of beneficial drug according to claim 1 wherein the drug is a pharmaceutically acceptable steroid.

7. A medicament for the management of cardiac decompensation, said medicament consisting essentially of (a) an adduct consisting of a digitaloid drug and a pharmaceutically acceptable nonionic surfactant, and (b) an osmotically effective solute which exhibits an osmotic pressure gradient across a semipermeable wall against an external fluid coated with the adduct, said medicament housed in an osmotic delivery system which system comprises (1) a shaped semipermeable wall permeable to the passage of fluid and impermeable to the passage of medicament, (2) the wall surrounding and forming a compartment housing the medicament, (3) a passageway in the wall communicating with the compartment and the exterior of the system, and (4) wherein in operation when the system is in a biological environment fluid from the environment is imbibed through the wall into the compartment forming a solution of adduct which solution containing the drug is released through the passageway at a controlled rate over a prolonged period of time thereby administering the drug for its intended beneficial effect.

8. The medicament for the management of cardiac decompensation according to claim 7 wherein the digitaloid drug is a cardiac glycoside.

9. The medicament for the management of cardiac decompensation according to claim 7 wherein the digitaloid drug is a member selected from the group consisting of acetyldigitoxin, deslanoside, digitalis, digitoxin, digoxin, gitalin, lanatoside, ovabain and mixtures thereof.

* * * * *